(12) United States Patent
Pursley

(10) Patent No.: US 7,445,684 B2
(45) Date of Patent: Nov. 4, 2008

(54) CATHETER HAVING FIBROUS REINFORCEMENT AND METHOD OF MAKING THE SAME

(76) Inventor: Matt D. Pursley, 430 Cameron Ct., Alpharetta, GA (US) 30022

( * ) Notice: Subject to any disclaimer, the term of this patent is extended or adjusted under 35 U.S.C. 154(b) by 661 days.

(21) Appl. No.: 10/735,352

(22) Filed: Dec. 11, 2003

(65) Prior Publication Data
US 2005/0131387 A1 Jun. 16, 2005

(51) Int. Cl.
 B21C 47/02 (2006.01)
 B29C 53/56 (2006.01)
(52) U.S. Cl. .................................... 156/172; 242/443
(58) Field of Classification Search ............... 264/134, 264/135; 604/526; 156/172; 242/443
See application file for complete search history.

(56) References Cited

U.S. PATENT DOCUMENTS

| | | | | |
|---|---|---|---|---|
| 3,701,489 A | * | 10/1972 | Goldsworthy et al. ... | 156/172 X |
| 4,484,586 A | * | 11/1984 | McMickle et al. ......... | 607/122 |
| 4,878,984 A | * | 11/1989 | Bourrieres ................. | 156/431 |
| 4,952,312 A | * | 8/1990 | Zantonelli et al. ....... | 210/321.74 |
| 5,888,436 A | * | 3/1999 | Keith et al. ................. | 264/103 |
| 6,030,371 A | * | 2/2000 | Pursley ....................... | 604/527 |
| 6,152,912 A | * | 11/2000 | Jansen et al. ................ | 604/526 |
| 6,511,462 B1 | * | 1/2003 | Itou et al. .................... | 604/264 |
| 2001/0041881 A1 | * | 11/2001 | Sarge et al. ................. | 604/525 |
| 2001/0044633 A1 | * | 11/2001 | Klint ........................... | 606/200 |

* cited by examiner

*Primary Examiner*—Leo B Tentoni
(74) *Attorney, Agent, or Firm*—Jeffrey L. Thompson; Thompson & Thompson, P.A.

(57) ABSTRACT

A catheter having a fibrous reinforcement is formed by anchoring a filament at a proximal end of a core member, and winding the filament onto the core member continuously from the proximal end to the distal end of the core member and then back to the proximal end to form a first fibrous layer. The filament is wound with a constant or variable pitch along the length of the core member. Additional fibrous layers can be applied by continuously winding a filament over the first fibrous layer from the proximal end to the distal end or to an intermediate position along the core member and then back to the proximal end. The additional layers can extend to different distal positions to form a catheter having a tapering profile. In alternative embodiments, catheters are formed by winding a group of filaments onto the core member simultaneously.

7 Claims, 5 Drawing Sheets

CATHETER HAVING FIBROUS REINFORCEMENT AND METHOD OF MAKING THE SAME

BACKGROUND OF THE INVENTION

1. Field of the Invention

The present invention relates generally to medical devices and, in particular, to medical catheters having fibrous reinforcement layers, and improved methods for making the same.

2. Description of the Related Art

Almost all medical catheters have fibrous reinforcement in the wall of the catheter. Usually the reinforcement is in the form of individual filaments, such as wires or small fiber bundles. These filaments are usually braided. Braiding has the disadvantage that the size of the filament is limited (i.e., if the filament is very small it tends to break during the braiding process).

Filament winding is also used to make catheters, as described in the Applicant's prior U.S. Pat. No. 6,030,371. There are many advantages to constructing catheters with a filament wound reinforcement. For example, it is possible to wind very small filaments (e.g., 0.0005" wires), which allows catheters to be constructed having a very small wall thickness.

FIGS. 1 to 4 show conventional process steps for making a filament wound catheter having a variable pitch. FIG. 1 shows a mandrel on which the catheter is formed; FIG. 2 shows the mandrel with a substrate placed thereon; and FIG. 3 shows the mandrel and substrate being rotated as a single filament is fed off a bobbin or spool and wrapped around the substrate. The single filament winding has a variable pitch over a length of the catheter, with the windings spaced closer together at a distal portion of the catheter as compared to a proximal portion of the catheter. FIG. 4 shows a cross section of the filament winding applied in a single pass over a length of the catheter. At the end of the single pass, the distal end of the filament either protrudes from the distal end of the substrate or is anchored thereto. The filament wound substrate shown in FIG. 4 is then coated with plastic (e.g., by applying a polymer in a particulate preform over the outer surface of the filament wound substrate, by laminating additional plastic tubes on top of the filament wound substrate, by extruding plastic over the filament wound substrate, or by applying the plastic as a molecular strand using electrostatic forces).

The catheter having a fibrous reinforcement formed by the process described above suffers from a number of disadvantages. For example, the filament tends to fray out of the wall or the distal end of the catheter and does not always remain intact during torque induced during use of the catheter. Thus, there is a need in the industry for an improved catheter having a fibrous reinforcement and methods of making the same.

SUMMARY OF THE INVENTION

It is an object of the present invention to provide an improved catheter having a fibrous reinforcement and methods for making the same.

It is a further object of the present invention to provide a catheter and improved methods of making the same in which a fibrous reinforcement layer is formed by a continuous filament having both its ends anchored in a proximal end of the catheter.

It is a further object of the present invention to provide a catheter and improved methods of making the same in which a fibrous reinforcement layer is formed by a continuous filament wound onto a core member with a variable pitch over a length of the catheter.

It is a further object of the present invention to provide a catheter and improved methods of making the same in which a plurality of fibrous reinforcement layers are formed in a staggered manner to form a catheter wall having a tapered profile.

It is a further object of the present invention to provide a catheter and improved methods of making the same in which groups of filaments are wound simultaneously onto a core member of the catheter to form a fibrous reinforcement layer.

To achieve the foregoing and other objects and in accordance with the purpose of the present invention, as embodied and broadly described herein, the method of making a catheter according to the present invention comprises: winding a filament onto a core member while rotating the core member relative to a filament source and passing the filament source in a first direction of axial movement relative to the core member; and reversing a direction of axial movement of the filament source while continuing to wind the filament onto the core member, whereby the filament is continuously wound onto the core member to form a first fibrous layer as the filament source is moved relative to the core member from a first axial position to a second axial position and then back to the first axial position.

According to another broad aspect of the present invention, a method of making a catheter is provided, comprising the step of winding a group of filaments simultaneously onto a core member while rotating the core member relative to a source of the filaments and passing the source of filaments in a first direction of axial movement relative to the core member.

According to another broad aspect of the present invention, a catheter is provided having a proximal end, a distal end, and a lumen extending between the proximal and distal ends. The catheter further comprises a fibrous reinforcement layer in a wall of the catheter comprising a continuous filament having first and second ends and a series of windings formed between the first and second ends. The first end of the filament is anchored in the proximal end of the catheter, the windings extend from the proximal end to the distal end of the catheter and then back to the proximal end, and the second end of the filament is anchored in the proximal end.

According to another broad aspect of the present invention, a catheter is provided having a proximal end, a distal end, a lumen extending between the proximal and distal ends, and a fibrous reinforcement layer in a wall of the catheter. The fibrous layer comprises a group of filaments which are wound around the lumen between the proximal and distal ends with a variable pitch.

Additional objects, advantages, and novel features of the invention will be set forth in the following description, and will become apparent to those skilled in the art upon reading this description or practicing the invention. The objects and advantages of the invention may be realized and attained by the appended claims.

BRIEF DESCRIPTION OF THE DRAWINGS

The present invention will become more clearly appreciated as the disclosure of the present invention is made with reference to the accompanying drawings. In the drawings.

DETAILED DESCRIPTION OF THE INVENTION

Catheters having improved fibrous reinforcement layers and methods of making the same according to the present invention will now be described with reference to FIGS. 1 to 15 of the accompanying drawings.

Figure 1:
FIG. 1 is a perspective view of a core mandrel on which a catheter can be formed.
Figure 2:
FIG. 2 is a perspective view of the mandrel and an inner liner of a catheter placed over the mandrel.

A method of making a catheter 10 having a fibrous reinforcement layer according to a first embodiment of the invention will be explained with reference to FIGS. 1 to 7. FIG. 1 shows a mandrel 11 on which the catheter 10 is formed. Those skilled in the art will understand that the catheter 10 can be formed directly on the mandrel 11, or on a core substrate 12 that forms an inner lining of the catheter 10 and is slid over the mandrel 11 as shown in FIG. 2. The phrase "core member" will be used in this application to refer to either the mandrel 11 or the substrate 12, whichever is used to form the core of the catheter 10.

Figure 3:
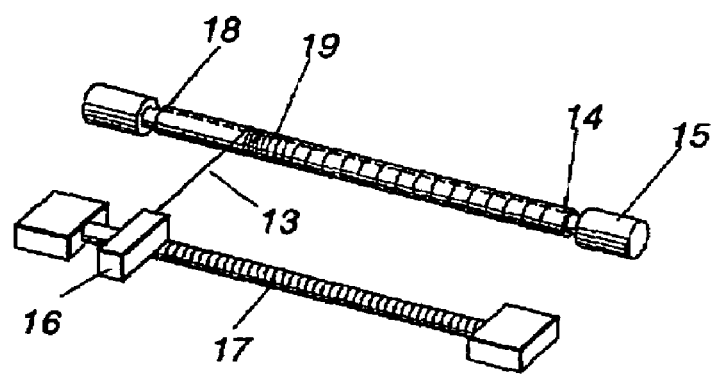
FIG. 3 is a perspective view of a single filament being wrapped with a variable pitch around the inner liner from the proximal end to the distal end as the mandrel is rotated.

FIG. 3 shows the process of winding a single filament 13 around the core member 12 (i.e., the substrate). The filament 13 is anchored at or near a proximal end 14 of the core member 12 before the winding starts. The core member 12 is then rotated about its longitudinal axis by a suitable apparatus 15. The filament 13 is fed onto the rotating core member 12 from a filament source 16, such as a filament spool or bobbin. The filament source 16 is moved along a guide 17 in a direction generally parallel to the longitudinal axis of the core member 12 from a starting position near the proximal end 14 of the core member 12 toward the distal end 18. The speed of rotation of the core member 12 and/or the speed of translation of the filament source 16 can be varied to change the pitch (i.e., turning angle) of the filament winding 19. For example, as the winding progresses along a length of the core member 12 toward the distal end 18, the pitch of the winding 19 can be changed so that the turns of the winding 19 are spaced differently near the proximal end 14 than near the distal end 18. In the portions of the catheter 10 that require high circumferential rigidity or kink resistance, the pitch can be changed to provide closely spaced turns of the filament 13, and in portions of the catheter that require low rigidity, the pitch can be changed to provide loosely spaced turns.

Although FIG. 3 shows a process in which the core member 12 is rotated about its axis and the filament source 16 is moved parallel to the core member 12, it will be understood by those skilled in the art that other methods of moving the core member 12 relative to the filament source 16 are also possible. For example, the core member 12 can be held stationary while the filament source 16 orbits around the core member 12 and also moves along a length of the core member 12 to wind the filament 13 on the core member 12. For another example, the filament source 16 can be held stationary while the core member 12 rotates about its axis and also moves in an axial direction. It will be understood that each of these process variations and others can be used to accomplish the desired relative movement between the core member 12 and the filament source 16.

Figure 4:
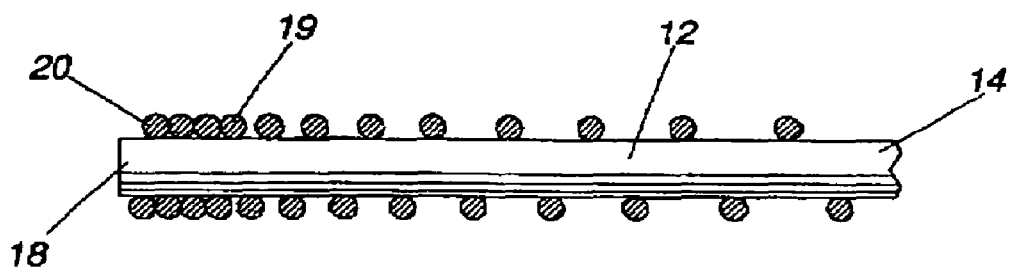
FIG. 4 is a cross section view of the inner liner with the variable pitch, single filament winding shown in FIG. 3.
Figure 5:
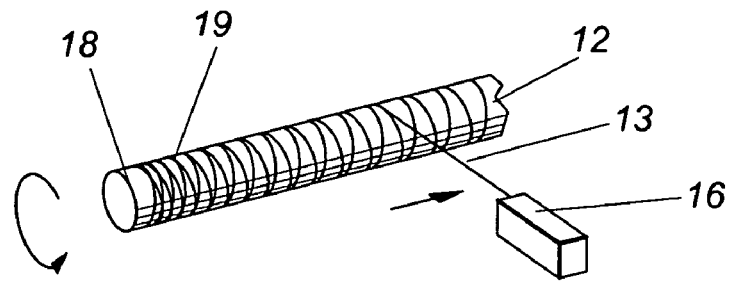
FIG. 5 is a perspective view of the inner liner having the single filament winding applied in a second pass from the distal end to the proximal end.
Figure 6:
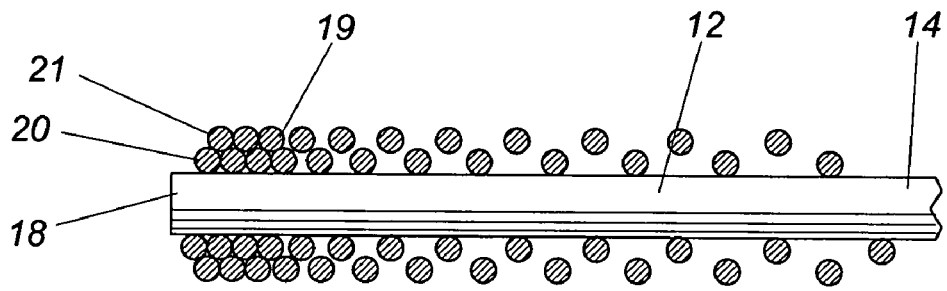
FIG. 6 is a cross section of the inner liner showing the second pass of the single filament winding.

Once the filament winding 19 reaches the distal end 18 of the core member 12 (the left side of FIG. 3), a first pass 20 of the filament winding 19 over the core member 12 is completed as shown in FIG. 4. As shown, the filament winding 19 can have a variable pitch in which the turns of the winding 19 become closer together near the distal end 18 of the core member 12. Alternatively, the filament winding 19 can have a constant pitch in which the turns of the winding 19 are evenly spaced over the entire length of the core member 12. When the first pass 20 is completed, the filament source 16 reverses its direction of axial movement while the core member 12 continues to rotate relative to the filament source 16. A second pass 21 of the filament winding 19 is then applied over the core member 12 (and over the first pass 20 of the filament winding 19) as the filament source 16 moves back toward the proximal end 14. As a result, the filament winding 19 is continuous from its initial anchor at the proximal end 14, to the end of the first pass 20 at the distal end 18 of the core member 12, and then back to the end of the second pass 21 at the proximal end 14. As shown in FIGS. 5 and 6, the second pass 21 of the winding 19 can be applied with a variable pitch similar to the first pass 20.

Figure 7:
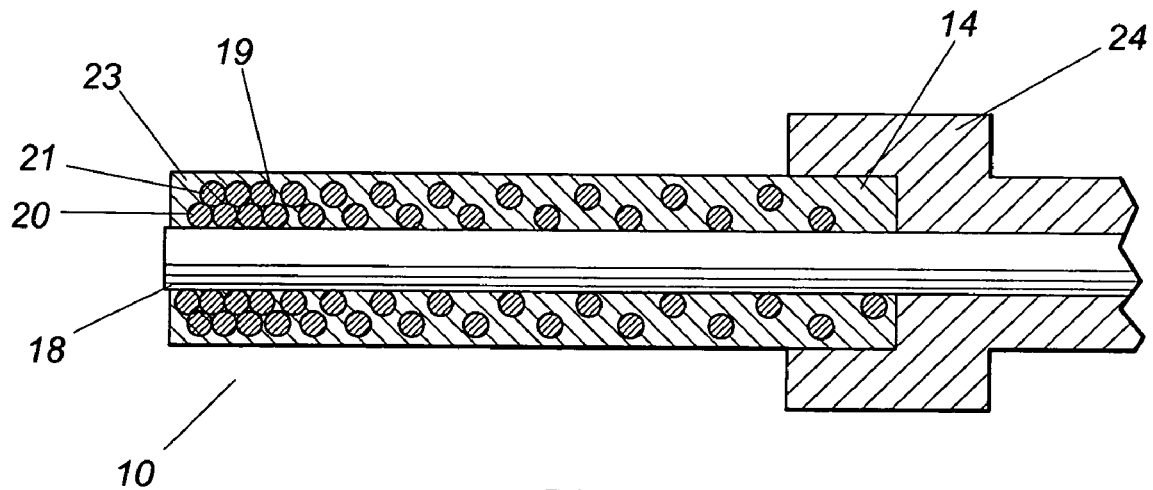
FIG. 7 is a cross section of the catheter with two passes of the filament winding and a plastic coating applied over the filament winding.

The first and second passes 20, 21 of the filament winding 19 together form a first fibrous layer 22 of the catheter 10. A plastic coating 23 is applied over the first fibrous layer 22 as shown in FIG. 7. The plastic coating 23 can be formed by applying a polymer material in a particulate preform over an outer surface of the core member 12 and the fibrous layer 22. A suitable process for applying the plastic coating in this manner is disclosed, for example, in the Applicant's U.S. Pat. No. 6,030,371, which is incorporated herein by reference. Alternatively, the plastic coating 23 can be applied by laminating a plastic tube over an outer surface of the core member 12 and the fibrous layer 22, or by extruding the plastic material over the fibrous layer 22, or by using electrostatic forces to apply the plastic material as a molecular strand using a nanospinning process. After the plastic coating 23 is applied, the proximal end 14 of the catheter 10 is anchored in a suitable hub 24.

Figure 8:
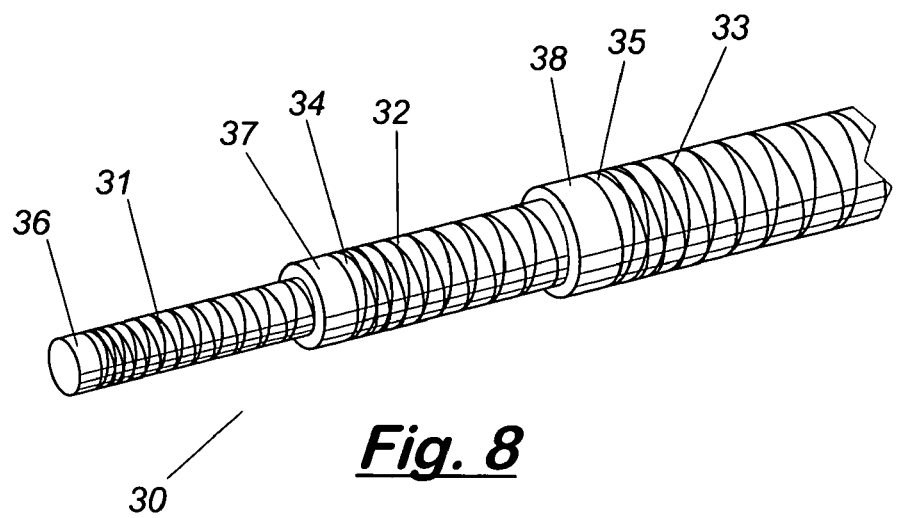
FIG. 8 is a perspective view of a catheter having additional layers of filament winding applied over the initial layer and marker bands at the distal ends of each layer.
Figure 9:
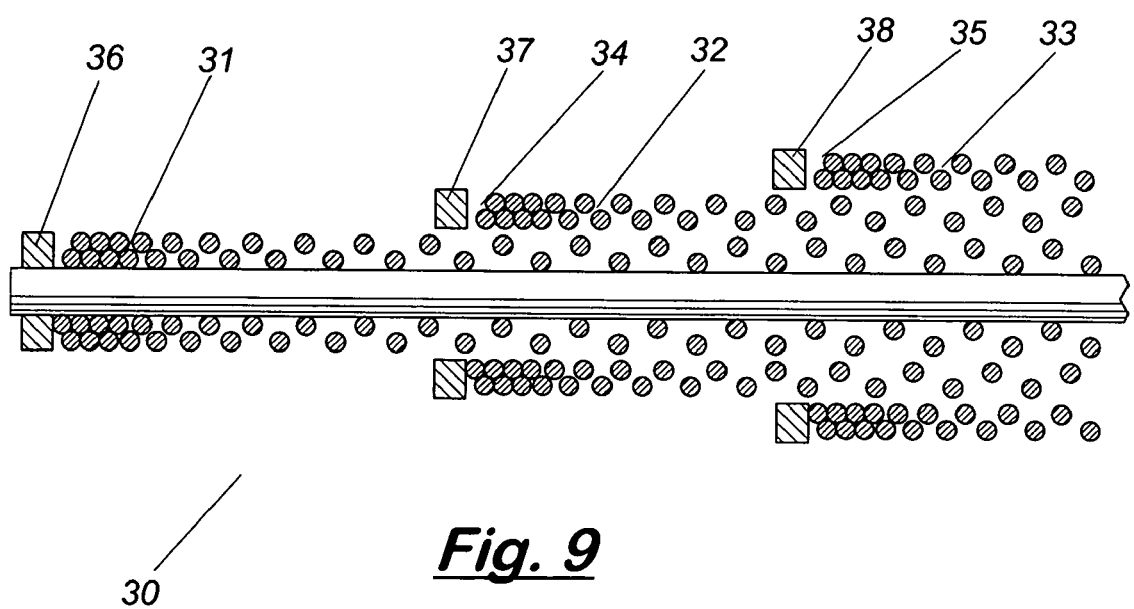
FIG. 9 is a cross section view of the catheter shown in FIG. 8.

As shown in FIGS. 8 and 9, a catheter 30 having multiple fibrous reinforcement layers 31, 32, 33 can be formed by repeating the process described above. Specifically, the first fibrous layer 31 of the catheter can be formed using the same process used to forming the first layer 22 in the above-described catheter 10. The additional fibrous layers 32, 33 can be applied over the first fibrous layer 31 to impart different properties along a length of the catheter 30. Each additional fibrous layer 32, 33 can be formed in a manner similar to the first layer 31. Specifically, the filament for the first additional layer 32 is anchored in the proximal end, and then the filament is wound over the first fibrous layer 31 as the filament source is moved axially along the core member from the proximal end to a distal position and then back to the proximal end.

The distal end 34 of the first additional layer 32 can be an intermediate point along the catheter 30 between the proximal and distal ends, as shown in FIGS. 8 and 9. The second additional layer 33 can be formed in a similar manner to the first additional layer 32. The distal end 35 of the second additional layer 33 can be at another intermediate point along the catheter 30. As shown in FIGS. 8 and 9, the additional layers 32, 33 can be progressively shorter than the first layer 31 so that the catheter 30 has a tapering profile and variable properties along its length. The pitch of the windings in each fibrous layer 31-33 can be varied as shown in FIGS. 8 and 9, or the pitch can be constant (not shown) so that the windings are spaced uniformly over a length of the catheter. A plastic coating can be applied over all of the fibrous layers 31-33 simultaneously, or the coating can be applied over each of the fibrous layers separately before the next fibrous layer is formed.

The end of each fibrous layer 31-33 provides an ideal location to place marker bands 36, 37, 38 for the catheter 30. The marker bands 36-38 are typically formed of thin metal and can be selected to have approximately the same thickness as the corresponding fibrous layer 31-33. For example, the fibrous layers 31-33 can each be formed using two passes of 0.0005 inch diameter filament, and the marker bands 36-38 can be formed using metal bands having a 0.001 inch thickness.

Figure 10:
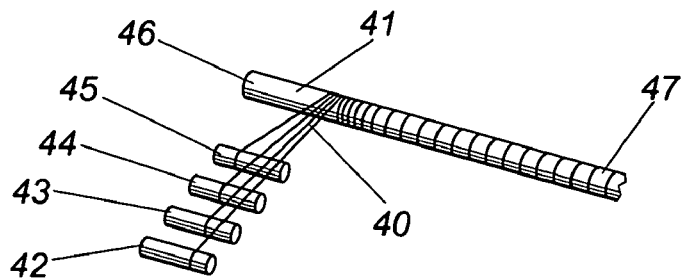
FIG. 10 shows the use of multiple bobbins to apply multiple strands of filament winding at the same time.

In another variation of the present invention, a group of filaments 40 are wound on the core member 41 simultaneously. As shown in FIG. 10, the group of filaments 40 can be supplied from a plurality of filament sources 42-45 (e.g., bobbins or spools). The filament sources 42-45 are moved in a controlled manner relative to the core member 41 so that windings having either a constant or a variable pitch can be applied over a length of the core member 41. For example, the group of filaments 40 can be wound with a variable pitch such that a filament group spacing at a distal end 46 of the core member 41 is narrower than a filament group spacing at a proximal end 47 of the core member 41, as shown in detail in FIG. 13.

The filament sources 42-45 can also be moved relative to each other to vary the spacing between the filaments within the group 40 as the winding progresses over a length of the catheter. For example, the filament spacing between the filaments within the group 40 at a distal end 46 of the core member 41 can be made narrower than the filament spacing at a proximal end 47 thereof. In still another embodiment, the group of filaments 40 can be wound with a variable pitch and a variable spacing between the filaments within the filament group 40.

Figure 11:
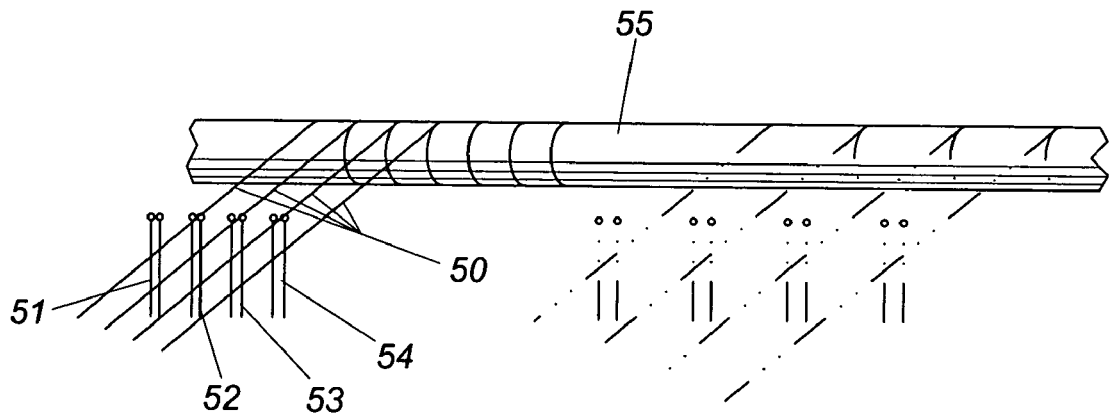
FIG. 11 shows the use of wire guides in conjunction with the multiple bobbins for varying the spacing between the filaments as the bobbins move along a length of the catheter.
Figure 12:
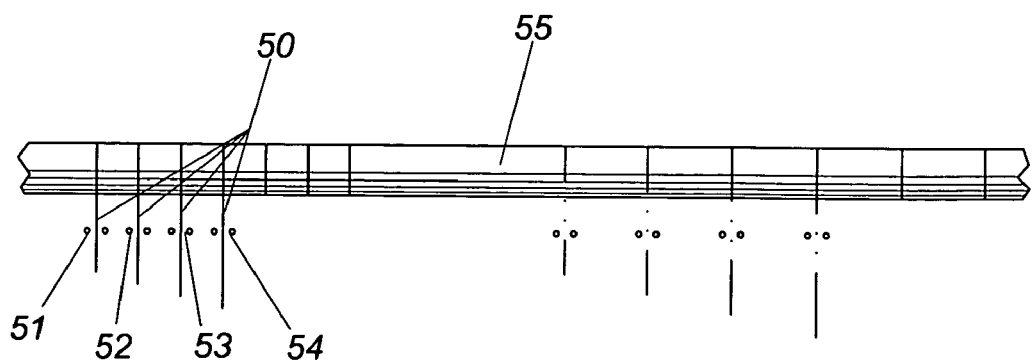
FIG. 12 is a plan view of the process shown in FIG. 11.

As shown in FIGS. 11 and 12, a plurality of wire guides 51-54 can be used to control the filament spacing within a group of filaments 50. In this case, the spacing between the wire guides 51-54 can be varied as the winding proceeds along a length of the core member 55 to change the filament spacing within the filament group 50. The use of wire guides 51-54 eliminates the slight fluctuations in spacing that would otherwise occur if the filaments were simply fed off of a spool or bobbin and directly onto the core member 55.

Figure 13:
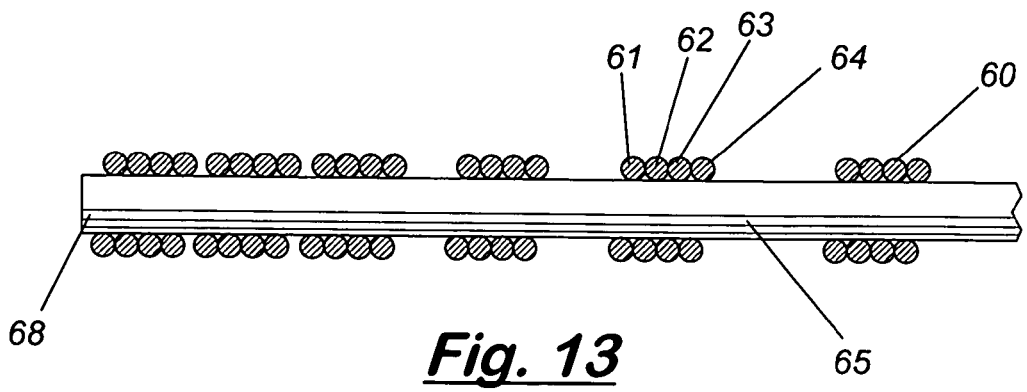
FIG. 13 is a cross section of a catheter having a bundle of filament wires wound about the inner lining with a closely packed filament spacing within the bundle and a variable pitch along the length of the catheter.
Figure 14:
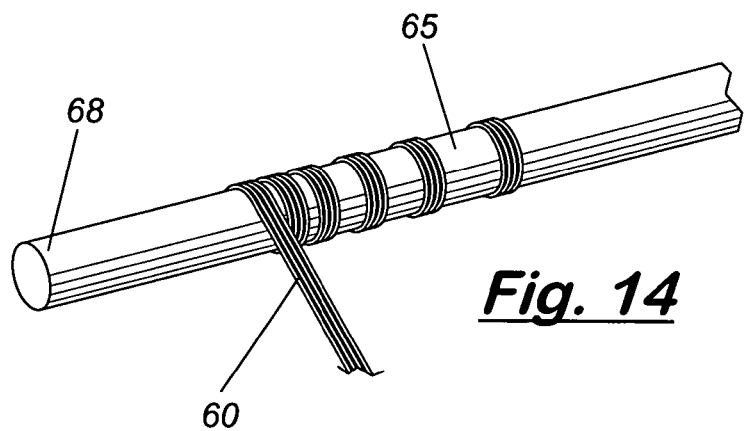
FIG. 14 is a perspective view of the bundle of filaments being applied to the catheter of FIG. 13.
Figure 15:
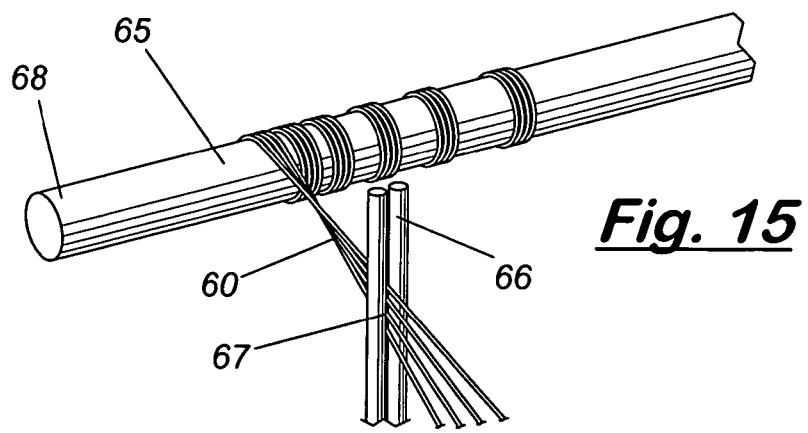
FIG. 15 is a perspective view of the catheter of FIGS. 13 and 14 with a wire guide assembly for guiding the bundle of filaments onto the catheter.

FIGS. 13 to 15 show an additional embodiment in which a group 60 of filaments 61-64 are wound onto the core member 65 in a close side-by-side arrangement. The closely packed group 60 is formed using a guide assembly 66, depicted in FIG. 15, which has a filament engaging surface 67 that lies in a plane generally perpendicular to a longitudinal axis of the core member 65. In this embodiment, the guide assembly 66 functions as the filament source. As the group 60 of filaments 61-64 pass through the guide assembly 66, the filaments 61-64 are arranged in a common plane which is approximately perpendicular to a plane containing the filaments 61-64 as they first engage an outer surface of the core member 65. For example, if the axis of rotation of the core member 65 is horizontal, the filament engaging surface 67 of the guide assembly 66 can extend along a vertical line.

The guide assembly 66 arranged in this manner causes the filaments 61-64 within the group 60 of filaments to be positioned side-by-side and packed tightly against one another as the group 60 of filaments are wound onto the core member 65. The pitch of the group 60 of filaments being wound onto the core member 65 can be varied by varying a rotation speed of the core member 65 and/or a translation speed of the guide assembly 66 as the filament source, in the manner described above.

The guide assembly 66 can be used to apply a group 60 of filament windings in two continuous passes to form a first fibrous layer over the outer surface of the core member 65. In this case, all of the ends of the filaments 61-64 can be anchored in the proximal end of the catheter, and the filaments 61-64 will be continuous at the distal end 68 of the catheter to avoid fraying and improving the performance of the catheter. Alternatively, the guide assembly and the other methods described herein for applying a group of filaments simultaneously can be used to form a fibrous layer in the catheter with a single pass over the core member and the distal ends of the filaments anchored at the distal end of the catheter.

Catheters having superior properties over the prior art can be formed by the methods described above. The catheters in each embodiment will have a proximal end, a distal end, a lumen extending between the proximal and distal ends, and at least one fibrous reinforcement layer in a wall of the catheter. The fibrous layer according to the preferred embodiment will have a continuous filament with first and second ends and a series of windings formed between the first and second ends. The first and second ends of the filament are anchored in the proximal end of the catheter, and the windings extend over a length of the catheter from the proximal end to the distal end. It will be understood that the catheters formed by each of the methods described herein are also considered part of the present invention.

While the invention has been specifically described in connection with specific embodiments thereof, it is to be understood that this is by way of illustration and not of limitation, and the scope of the appended claims should be construed as broadly as the prior art will permit.

What is claimed is:
1. A method of making a catheter, comprising the steps of:
winding a filament onto a core member while rotating the core member relative to a filament source and passing the filament source in a first direction of axial movement relative to the core member; and
reversing a direction of axial movement of the filament source while continuing to wind the filament onto the core member, whereby the filament is continuously wound onto the core member to form a first fibrous layer as the filament source is moved relative to the core member from a first axial position to a second axial position and then back to the first axial position;

wherein said step of winding a filament comprises winding a group of filaments simultaneously;

further comprising the step of providing a guide assembly having a filament engaging surface, and arranging said guide assembly such that the filament engaging surface lies in a plane which is generally perpendicular to a longitudinal axis of the core member; and further comprising the step of passing the group of filaments through the guide assembly to arrange the group of filaments into the plane which is generally perpendicular to the longitudinal axis of the core member and to cause the filaments within said group of filaments to be positioned side-by-side and packed tightly against one another as the group of filaments are wound onto the core member;

further comprising the step of anchoring the group of filaments at or near a proximal end of the core member before winding the group of filaments onto the core member.

2. The method of making a catheter according to claim 1, wherein the group of filaments is wound onto the core member continuously from the proximal end of the core member to a distal end thereof and then back to the proximal end.

3. The method of making a catheter according to claim 1, wherein the core member is a mandrel on which the catheter is formed.

4. The method of making a catheter according to claim 1, wherein the core member is a substrate that forms an inner lining of the catheter.

5. The method of making a catheter according to claim 1, wherein said group of filaments are wound with a variable pitch such that a filament group spacing at a distal end of the core member is narrower than a filament group spacing at a proximal end of the core member.

6. The method of making a catheter according to claim 1, further comprising the step of varying a rotation speed of the core member or a translation speed of the filament source along the core member to vary a pitch of the group of filaments being wound onto the core member.

7. A method of making a catheter, comprising the steps of:

anchoring a group of filaments to a core member at a proximal end of the catheter;

winding the group of filaments simultaneously onto the core member while rotating the core member relative to a filament source and passing the filament source in a first direction of axial movement relative to the core member toward a distal end of the catheter; and reversing a direction of axial movement of the filament source while continuing to wind the group of filaments simultaneously onto the core member, whereby the group of filaments are continuously wound onto the core member to form a fibrous layer as the filament source is moved relative to the core member from the proximal end to the distal end and then back to the proximal end;

further comprising the step of passing the group of filaments through a guide assembly to arrange the group of filaments into a plane which is generally perpendicular to a longitudinal axis of the core member and to cause the filaments to be positioned side-by-side and packed tightly against one another as the group of filaments are wound onto the core member.

* * * * *